United States Patent [19]

Kosuge et al.

[11] Patent Number: 5,632,997
[45] Date of Patent: May 27, 1997

[54] METHOD OF TREATING LIVER DISFUNCTION IN MAMMALS, USING ACTIVE PRINCIPLE ISOLATED FROM SHARK TISSUE

[75] Inventors: Takuo Kosuge; Kuniro Tsuji; Hitoshi Ishida; Yoshiki Kosuge, all of Shizuoka, Japan

[73] Assignee: J. W. Broadbent Nominees Pty. Ltd., Melbourne, Australia

[21] Appl. No.: 468,977

[22] Filed: Jun. 6, 1995

Related U.S. Application Data

[62] Division of Ser. No. 169,761, Dec. 20, 1993, Pat. No. 5,470,574, which is a continuation of Ser. No. 818,470, Jan. 6, 1992, abandoned, which is a continuation of Ser. No. 622,013, Jan. 14, 1991, abandoned, which is a division of Ser. No. 328,040, Mar. 29, 1989, Pat. No. 5,026,883.

[30] Foreign Application Priority Data

Aug. 21, 1986 [AU] Australia ............... PH7614/86

[51] Int. Cl.$^6$ ............... A61K 9/48; A61K 35/60
[52] U.S. Cl. ............... 424/401; 424/554; 514/893; 514/894; 552/542
[58] Field of Search ............... 514/893, 894; 424/554, 401; 552/542

[56] References Cited

U.S. PATENT DOCUMENTS

| | | | |
|---|---|---|---|
| 2,136,453 | 11/1938 | Merker | 260/412.1 |
| 3,994,878 | 11/1976 | Partridge | 549/554 |
| 4,296,109 | 10/1981 | Laurent et al. | 514/173 |
| 5,026,883 | 6/1991 | Kosuge | 552/542 |

FOREIGN PATENT DOCUMENTS

| | | |
|---|---|---|
| 0131659 | 3/1949 | Australia . |
| 0034912 | 3/1978 | Japan . |
| 0079012 | 7/1978 | Japan . |
| 0081610 | 7/1978 | Japan . |
| 0044011 | 4/1979 | Japan . |
| 0031619 | 2/1982 | Japan . |
| 0170718 | 10/1983 | Japan . |
| 0020201 | 2/1984 | Japan . |
| 0033121 | 2/1986 | Japan . |

OTHER PUBLICATIONS

Honma et al, "Rep Sado Mar Biol Stn Nigata Univ", Biological Abstracts, 86(1):AB–399, 1988 Abstract 3404.

Snyder and Kirkland, Introduction to Modern Liquid Chromatography (New York: J. Wiley and Sons, Inc.), 1979, p. 477.

*Primary Examiner*—Sallie M. Gardner
*Attorney, Agent, or Firm*—Cushman Darby & Cushman IP Group of Pillsbury Madison & Sutro LLP

[57] ABSTRACT

A compound of general formula, in substantially pure form, wherein A is a cation. A method for preparation is also disclosed, together with compositions and methods of use thereof. The active principle, isolated from shark tissue, is used for treating liver disfunction, or protecting liver function, in mammals.

6 Claims, No Drawings

METHOD OF TREATING LIVER DISFUNCTION IN MAMMALS, USING ACTIVE PRINCIPLE ISOLATED FROM SHARK TISSUE

REFERENCE TO RELATED APPLICATIONS

This is a division of application No. 08/169,761, filed Dec. 20, 1993, (now U.S. Pat. No. 5,470,574) which was a continuation of application No. 07/818,470, filed Jan. 6, 1992 (abandoned), which was a continuation of application No. 07/622,013, filed Jan. 14, 1991 (abandoned), which was a division of application No. 07/328,040, filed Mar. 29, 1989 (now U.S. Pat. No. 5,026,883, issued Jun. 25, 1991).

BACKGROUND OF THE INVENTION

This invention relates to the identification, isolation and preparation of an active principle by extraction from natural tissues, and in particular it relates to the identification, isolation and preparation of such an active principle by extraction from particular tissues of sharks.

In Japan, a preparation known as "deep-sea shark liver oil" has been used as a folk remedy for a long time. It is an oil prepared from shark's liver and is normally capsulated in soft capsules. The liver oil is said to be effective in treatment of many kinds of diseases, especially those which are related to the liver, such as hepatitis, nephritis, diabetes, etc. As well, when used externally, it is widely recognised that the liver oil is effective in treatment of scalds, burns or other types of skin trouble, and also is ideal as an ingredient for cosmetics.

SUMMARY OF THE INVENTION

The present inventors have been studying this material for many years, and recently have discovered the unexpected fact that an active substance exists in the aqueous component of shark's liver rather than the oil soluble component. This fact was recognised from a comparison of the practical use of the liver oil and a powder produced from the aqueous component of the liver by evaporation of the water. In comparative tests of a dosage of 900 mg of the liver oil per day and 60 mg of the powder per day, the latter gave a better clinical result than the former. Furthermore, where the liver oil was thoroughly washed with water, the resulting oil showed almost no effect. These facts indicate that the active substance of deep-sea shark liver is not oil-soluble as previously believed, but is water-soluble.

According to the present invention, there is provided an active principle which is isolated from an aqueous extract of the liver and/or gallbladder of a shark.

In a first aspect of the invention, there is provided a compound of the general formula I, in substantially pure form,

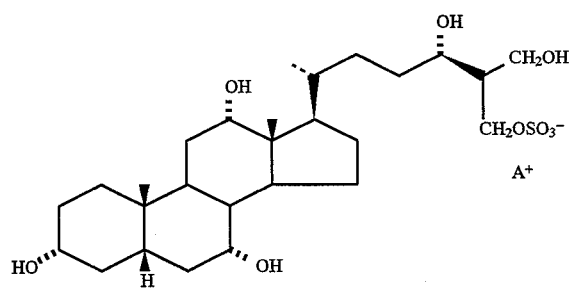

wherein A is a cation, such as a sodium, potassium, calcium or ammonium ion, or an organic amine.

In other aspects, this invention provides a method for the preparation of a compound of general formula I in substantially pure form, together with compositions for pharmaceutical, dietary or cosmetic purposes which comprise such a compound.

By using activity assays which are described in detail below, it has been shown that the active principle is water-soluble and does not exist in the oil-soluble component of shark's liver. These assays have been used in a series of tests to ascertain whether the active principle exists only in the liver. All parts of the shark's body, such as the bones, meat, gallbladder, ovary, alimentary canal, etc., have been investigated, and it has been found that the gallbladder showed the same activities as liver in the assays. This result indicates that the active principle exists only in liver and gallbladder.

In general terms, the two bioassays referred to herein and used to identify sources of the active principle and to assess the degree of purity of an extract, are designed to identify characteristic pharmacological activities of the substance. In particular, the bioassays, designated as (A) and (B) are based on the following activities:

(A) The active principle prevents liver trouble in mice caused by carbon tetrachloride.

(B) The active principle increases the respiration rate in mice when a toxic substances such as nicotine is administered.

The present invention also provides a method for preparing an active principle as described above, which comprises the steps of preparing an aqueous extract of the liver and/or gallbladder of a shark, and isolating the active principle from the aqueous extract.

DETAILED DESCRIPTION

The following description sets out general procedures for isolation of the active principle from the aqueous extract of the liver and/or gallbladder of a shark, involving the steps of extraction with polar organic solvents, adsorption on suitable adsorbents and/or chromatography techniques.

In order to determine whether the active principle is soluble in polar organic solvents, such as methanol, ethanol, acetone, etc., the powder obtained by freeze-drying of shark's bile was extracted with polar organic solvent, then the (A) and (B) assays were applied to both the soluble part and the insoluble part. Activity was seen only in the assays on the soluble portion, thus establishing that active principle is soluble in polar organic solvents.

In testing to determine whether the active principle can be isolated utilising adsorbents, many adsorbents were examined and it was found that the active principle can be adsorbed by ion exchange resins of basic anion exchange type, or by synthetic adsorbents such as XAD, HP-20, Sep-pak c18, etc., or charcoal. This absorption test was performed by extracting shark's liver and/or gallbladder with water. Each adsorbent under test was added to the extract and left to stand overnight. The mixture was then filtered and each filtrate tested for activity by the (A) and (B) assays. The results indicate that the active substance is adsorbed by those adsorbents mentioned above. The active principle may be recovered from the adsorbent resins by extraction with acid, alkali or salts, and from the synthetic adsorbents and charcoal by extraction with polar organic solvents.

Further purification of the active principle is achieved by chromatography, for example in a silica column, SephadeX LH-20 column, or by preparative TLC (thin layer chromatography) or HPLC (high performance liquid chromatography), etc. Each method gave satisfactory results, but HPLC gave the best purification. The active principle as isolated by HPLC was quite pure because it gave very sharp single peak and also gave a single spot of approximate representative Rf Value of 0.36 on TLC. The active principle in its purified form is a white powder of melting point of 140° C.

Testing of the purified active principle by vanillin sulfuric acid gave a purple colour, indicating that it contains bile acid or bile alcohol in its structure. It has already been found that the bile of sharks contains a bile alcohol named scymnol. After partial acetylation of the active principle with acetic anhydride, followed by treatment of the crude product with dry dioxan-trichloroacetic acid for several days, scymnol was identified from the reaction mixture. The result indicated that the active principle is a scymnol derivative. It was the first isolation of the pure scymnol derivative contained in bile of shark, as the active principle.

A preferred procedure for isolation of the actave principle from the lyophilized bile of *Rhizoprinodon acutus* (obtained by homogenization and freeze-drying of gall-bladders), is set out in the following chart:

Lyophilized bile of *Rhizoprionodon acutus* extracted with
1. n-Hexane (100 ml×3)
2. MeOH (100 ml×3)

Fraction I (MeOB-extract)
1. dissolved in $H_2O$
2. AmberAirs XAD-2 c.c., eluting with
   i. $H_2O$ (400 ml)
   ii. MeOH (400 ml)

Fraction II (MeOH-eluate)
1. dissolved in $CHCl_3$-MeOH(1:1)
2. Sephadex LH-20 c. c. eluted with
   i. $CHCl_3$-MeOH(1:1) (300 ml)
   ii. MeOH (500 ml)

Fraction III
HPLC: YMC.-Pack A-324 (ODS)
Colorless powdex (compound I)

As set outabove, in this procedure the lyoophilized material is deflated with n-hexane, and then extracted with methanol. The concentrate thus obtained is applied to an Amberlite XAD-2 column in batches, using $H_2O$, and ethanol as eluents. As the ethanol eluate contains the active principle (as determined by color teagent), this fraction is successively subjected to gel filtration on Sephadex LH-20 with chloroform-methanol and methanol. The active principle is so effectively contained in the methanol eluate that its final purification is achieved by successive application of HPLC with a reverse phase column.

It has been suggested that scymnol might be in the form of a sulphate ester, but no positive information has been published about the position of attachment of the sulphate ester, because scymnol has six hydroxyl groups where the sulphate ester group might be attached. The present scymnol derivative has never been isolated as a pure substance. The active powder as purified by HPLC was subjected to elementary analyses. Results were anal: calcd for $C_{27}H_{51}O_9NS$, C;57.34, H;9.02, N;2.47, S;5.66. Found C;57.23, H;8.92, N;2.45, S;5.30. These results suggested that the active compound has ammonium sulphate ester in the structure. Nuclear magnetic resonance spectroscopy of the active powder showed the following properties.

$^1H$-NMR(in $d_4$-MeOH) δ(ppm): 4.22(dd, 1H, J=4.5 and 10.0 Hz), 4.11(dd, 1H, J=10.0 and 16.7 Hz), 4.00(bs, 1H), 3.80 (d, 1H, J=1.2 Hz), 3.60–3.80(m, 4H), 3.30–3.45(m, 1H), 0.72(s, 3H).

$^{13}C$-NbLR(in $d_4$-MeOH) δ (ppm): 74.1 (d), 72.9 (d), 71.3(d), 69.1(d), 66.7(t), 61.2(t), 48.4(d), 47.8(d), 47.5(s), 43.1(d), 43.0(d), 41.0(d), 40.4 (t), 37.0 (d), 36.5 (t), 35.9 (s), 35.8 (t), 33.3(t), 32.1(t), 31.2(t), 29.6(t), 28.8(t), 27.9(d), 24.3(t), 23.2(q), 18.1(q), 13.1(q).

$^{13}C$-NMR spectrum shows that the active compound has 27 carbon atoms made up of three methyl, 11 methylene, 11 methine and two tertiary carbons. The signals at low field (0.72–2.35) in $^1H$-NMR spectrum suggest that it seems to be a coprostane derivative. At the higher field in $^{13}C$-NMR spectrum, signals at 74.1(d), 72.9(d), 71.3(d) and 69.1(d) are assignable to the methine carbon with hydroxyl group. And the two signals at 66.7(t) and 61.2(t) are ascribable to the O-substituted methylene carbon. 2D0COSY0NMR spectra and C–H-shift-COSY relationship indicate that these two carbons attach to a methine carbon and one of them with low chemical shift (66.7) has two unequivalent protons at 4.22 (dd) and 4.14(dd)ppm in the $^1H$-NMR spectrum, which indicates that the active compound has the partial moiety of $HOCH_2$—CH—$CH_2OR$ in the molecule. From the results of elementary analyses, R is —$SO_3NH_4$.

From these NMR spectra and elementary analyses, the powder is characterised as 3α,7α, 12α, 24ε, 26-pentahydroxycoprostane-27-ammonium sulphate ester. The ammonium ion in the structure possibly came from the phosphate ammonium buffer used as mobile phase in HPLC, by replacement of a sodium ion. To verify this point, an active powder purified by XAD-2 and then by column chromatography on Sepadex LH-20 was subjected to atomic absorption spectrophotometry for sodium and to elementary analysis for nitrogen. The results were, calcd. for $C_{27}H_{47}O_9SNa$, Na;4.03, N;0.00, found Na;3.57, N;0.02. The stereochemistry of the C-24 position in the structure was determined as 24R by X-ray crystallographic analysis of scymnol and the specific rotation of sodium scymnol sulphate is positive. Accordingly, it is concluded that the active principle isolated from shark is 24R-(+)-3α,7α,12α,24,26-pentahydroxycoprostane-27-scdium sulphate ester.

The sodium or ammonium ion in the sulphate ester is easily replaced by other metal ions such as potassium, calcium, etc., or by organic amine cations such as amino acids, etc., by means of well known procedures.

The following Tables illustrate the activity of the aqueous extracts of this invention:

TABLE I

|  | Dosage | Bioassay(A) (Units) | Bioassay(B) (Seconds) |
|---|---|---|---|
| Oil-soluble part of shark's liver | 500 mg | 13,800 | 21 |
| Water-soluble part of shark's liver | 50 mg | 9,500 | 15 |
| Control |  | 13,000 | 22 |

TABLE II

| Aqueous Extract of Shark's Gallbladder, Purified by: | Dosage | Bioassay(A) (Units) | Bioassay(B) (Seconds) |
|---|---|---|---|
| Charcoal adsorption | 5 mg |  | 15 |
| XAD-2 adsorption | 1 mg |  | 16 |
| Anion-exchange resin adsorption | 0.5 mg | 8,200 | 14 |
| Purified active principle | 0.15 mg | 9,600 | 15 |
| Control |  | 14,000 | 22 |

Standard bioassays referred to in the above description were performed as follows:

Bioassay (A)

Biological test for protective activity against carbon tetrachloride ($CCl_4$)-induced liver lesions in mice.

Male Std:ddy mice (weight 30–35 g) were used in groups of 5 animals. Samples of test materials were administered orally 7 days at a suitable daily dose and 0.1 ml of 5% $CCl_4$ in olive oil was orally administered at 24 hrs after the last sample administration. Blood was obtained from the orbital sinus at 24 hrs after the $CCl_4$ administration. Serum was obtained by centrifugation (3,000 rpm., 10 min) and glutamic pyruvic transaminase (GPT) activity was measured by Reitman-Frankel-Momose method. Activity was expressed as a comparison of GPT values between the sample-administered groups and controls.

Bioassay (B)

Effect on respiration in nicotine administration to mice.

Male Std:ddy mice (weight 20–22 g) were used in groups of 5 animals. Nicetine tartrate (3mg) was injected subcutaneously. Samples of test materials were orally administered 3hrs before nicotine administration. The time taken for 30 respirations was counted 5 minutes after nicotine administration. Activity was expressed as a comparison of the counted time between the sample-administered groups and controls:

The present invention also provides a pharmaceutical composition comprising an active substance as described above, together with a pharmaceutically acceptable carrier or diluent therefor. By way of example, the active substance can be formulated as stable tablets after being mixed as a powder with a known carrier or bulking agent. Alternatively, the active substance can be incorporated into a lotion or cream base for topical application. In yet another alternative, the active substance can for example be filled in soft gelatin capsules, if desired after being admixed with shark's liver oil. Such pharmaceutical compositions may be used, for example, for the protection of the liver or activation of liver function in the treatment of diseases or conditions affecting the liver such as hepatitis, nephritis, diabetes, etc.. Such compositions may also be used for the activation of regeneration of skin tissue, for example, in the treatment of dermatitis, trauma or ache.

Clinical tests which have been performed using compositions containing the active substance have specifically demonstrated its activity in restoration of the liver function, and in the treatment of seborrhea.

In a further aspect of this invention, there is provided a dietary or health food composition which comprises the active principle described herein, together with one or more appropriate base or carrier materials. Such a composition may, for example, be useful in the treatment of a hangover.

In another aspect, the present invention provides a cosmetic composition comprising the active principle as described above, together with a cosmetic base material.

The compositions of the present invention may also incorporate known pharmaceuticals or other active ingredients, for example, antibiotics or other antibacterial substances.

Further details of this invention will be apparent from the following Examples which illustrate the invention without limiting it in any way.

EXAMPLE 1

Preparation of Crude Active Principle 280 g of a mixture of liver and gallbladder isolated from 4 kg of shark was homogenised in 300 ml of water, and the mixture was centrifuged at 12,000 rpm for 30 minutes to obtain a clear aqueous layer. 50 g of ion exchange resin of basic anion exchange type was added to the aqueous layer and the mixture was left to stand overnight. The resin was removed by filtration and washed with water. The resin was then extracted with 200 ml of 0.5% sodium chloride solution. 100 g of XAD2 was added to the extracted solution. XAD2 was removed by filtration and washed with water. XAD2 was extracted with 200 ml of ethanol. From the extract, ethanol was removed by distillation to obtain 45 mg of crude active powder.

EXAMPLE 2

Silica gel column chromatography 100 g of crude active compound obtained by adsorption on a XAD-2 column was subjected to chromatography on a silica gel column, using MeOH-$CHCl_3$-$H_2O$(30:70:6) as solvent, to afford white powder (40 g).

EXAMPLE 3

Thin layer chromatography (TLC)

Crude active compound was subjected to TLC on a precoated silica gel 60 thin layer plate (Merck), using the system (parts by volume):

n-BuOH(85)-AcOH(10)-$H_2O$(5) and MeOH(40)-$CHCl_3$(60)-$H_2O$(10). The active principle showed as a single spot on TLC, and was visualized by spraying with vanillin sulfuric acid reagent.

EXAMPLE 4

High performance liquid chromatography (HPLC)

Final purification of crude active powder was achieved by successive application of preparative HPLC with a reverse phase column. 31 g of the active compound in the form of white powder, mp.140°, was obtained from 100 g of XAD-2 purified sample. The approximate representative retention time of the active compound was 16 minute. The conditions for HPLC were as follows: column: YMC-Pack A-324 (ODS); flow rate: 20 mi/min.; mobile phase: $CH_3CN$-0.02N phosphate ammonium buffer (pH 7.45)(8:2); detector: refractive index.

EXAMPLE 5

Column chromatography on Sephadex LH-20

Crude active compound (100 g) obtained by adsorption on a XAD-2 column was subjected to gel filtration on Sephadex LH-20 column, using MeOH-$CHCl_3$(1:1) and then MeOH as eluents, to afford white powder (45 g) from the MeOH fraction. Rechromatography on the same column afforded 30 g of almost pure white powder.

EXAMPLE 6

Gall-bladders (65 g), obtained from 5 sharks of the species *Rhizoprionedon acutus* (ca 8 Kg weight), were homogenized and then freeze-dried. This material (10.25 g) was used as a source of the active principle, sodium scymnol sulphate. After defatting the material with refluxing n-hexane (100 ml ×3), it was extracted with methanol (100 ml ×3) under reflux for 1 h. The concentrate (3.67 g) was dissolved in $H_2O$ (80 ml), and applied to an Amberlite XAD-2 column (3.0×16.0 cm). The column was eluted with $H_2O$ (400 ml) and then with ethanol (400 ml). Then, the ethanol eluate (1.95 g) was applied to Sephadex LH-20 column (3.0×32.0 cm), chloroform and methanol (1:1). After elution with chloroform and methanol (200 ml), the column was developed with methanol in batches of 50 ml. Concentration of the methanol eluate containing the sodium salt gave a white gum (1.06 g). Purification of this material (120 mg) by HPLC yielded 85.6 mg of sodium scymnol sulphate as white powder. The conditions for HPLC were as follows: column, YMC-Pack A-324(ODS) 10×300 mm; flow rate, 2 ml/min; mobile phase, 35% $CH_3CN$-0.1N Sodium Phosphate Buffer (pH 6.43); detector, Refractive Index. Sodium scymnol sulphate has the following physical data: White powder; $[\alpha]_D^{25}$=21.75 (0.5 c. in MeOH); Anal.: Calcd. for $C_{27}H_{47}O_9SNa$: C;56.82 H;8.30 S;5.62 Na;4.03. Found: C;56.99 H;8.79 S;5.62 Na;4.23. SIMS mass (m/e): 654 $[C_{97}H_{47}SO_9.HN(C_2H_6O)_2.]$574$[C_{27}H_{47}O_6$-$HN(C_2H_6O)_2$. IRv$_{max}^{KBr}$ cm$^{-1}$: 3420, 2950, 1470 1380 1230 1070 980 910, 810. $^1$H-NMR (in $CD_3OD$); δ (ppm): 4.22(1H,dd,J= 4.5, 10.0 Hz), 4.11(1H,dd,J=6.6, 10.0 Hz), 4.00 (1H, broad) , 3.80 (1H, m) , 3.80–3.62(3H, m), 3.45–3.30(1H, m), 2.35–2.15(2H, m), 2.05–1.02(23H, m), 1.02 (3H, d, J=6.2 Hz), 0.92 (3H, s), 0.72 (3H, s). $^{13}$C-NMR (in $CD_3OD$); δ (ppm): 74.1 (d) , 72.9 (d), 71.4(d), 69.1(d), 66.7(t), 61.2(t), 48.3(d), 47.8(d), 47.5 (s), 43.1 (d), 43.0 (d), 41.0 (d), 40.3 (t), 37.0 (d), 36.5(t), 35.9(s), 35.8(t), 33.3(t), 32.1(t), 31.2(t), 29.5(t), 28.8(t), 27.9(d), 24.3(t), 23.2(q), 18.1,(q), 13.1(q).

EXAMPLE 7

Trials have been conducted using the active principle of this invention in an antiseborrheous lotion applied topically by 40 male and female patients affected by long established (72) years facial hyperseborrhea. The trials were conducted as double blind trials with 20 patients applying a placebo and 20 patients applying the lotion containing the active principle.

In these trials, the treatment was applied three times daily (morning, midday and evening) over a period of 20 days, and an evaluation of seborrhea (Seborrhea Index) made at days 0, (prior to treatment), 10 and 21, (at end of treatment).

The results showed a significantly greater improvement in the seborrhea for patients using the lotion containing the active principle than for patients using the placebo. It was also observed that this improvement was shown in both male and female patients.

EXAMPLE 8

Compositions
1. Cold cream
   Spermacetti 6.0 g
   Beeswax 6.0 g
   Carbopol 9.34 10.0 g
   Sodium Carbonate 4.75 g
   Rose water 5.0 ml
   Rose oil 0.02 ml
   Expressed almond oil 56.0 g
   Active principle 0.05 g
   Distilled water 20.0 g
2. Tonic
   Ethanol 30 ml
   Active principle 20 mg
   Flavour q.s.
   Distilled water—sufficient quantity to make 100 ml

We claim:

1. A method of treating liver dysfunction, comprising administering to a mammal in need of such treatment a purified form of a compound of the general formula I

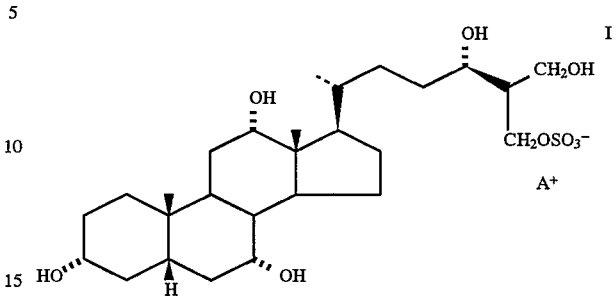

wherein A is a cation selected from the group consisting of sodium, potassium, calcium, ammonium or an organic amine; said purified form of said compound producing a single peak upon chromatographic analysis, and said compound being administered in an amount sufficient to effect said treatment.

2. A pharmaceutical composition for the treatment of liver dysfunction, consisting essentially of a purified form of a compound of the general formula I

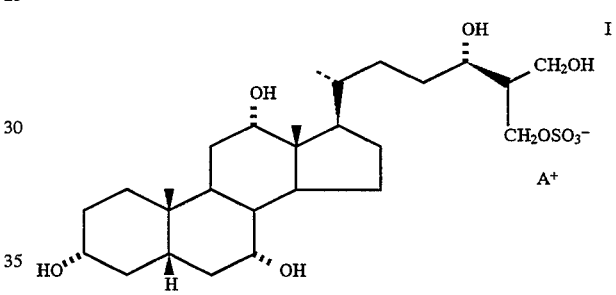

wherein A is a cation selected from the group consisting of sodium, potassium, calcium, ammonium or an organic amine; said purified form of said compound producing a single peak upon chromatographic analysis, and said compound being present in an amount sufficient to effect said treatment; together with a pharmaceutically acceptable carrier or diluent therefor other than water alone.

3. The composition of claim 2 in the form of a tablet or soft gelatin capsule.

4. A method of treating at least one of hepatitis, nephritis or diabetes comprising administering to a mammal in need of such treatment a purified form of a compound of the general formula I

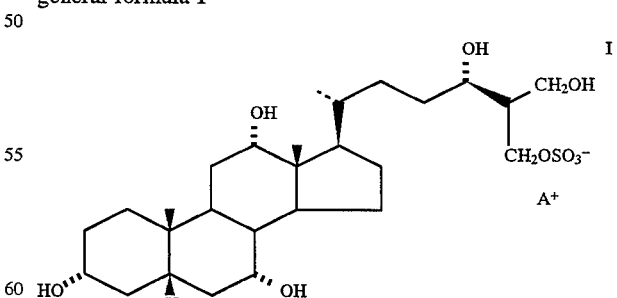

wherein A is a cation selected from the group consisting of sodium, potassium, calcium, ammonium or an organic amine; said purified form of said compound producing a single peak upon chromatographic analysis, and said compound being administered in an amount sufficient to effect said treatment.

5. A pharmaceutical composition for the treatment of at least one of hepatitis, nephritis or diabetes, consisting essentially of a purified form of a compound of the general formula I

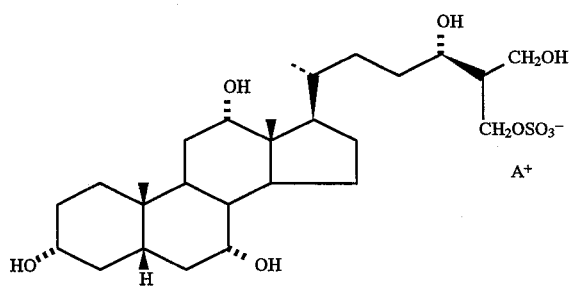

wherein A is a cation selected from the group consisting of sodium, potassium, calcium, ammonium or an organic amine; said purified form of said compound producing a single peak upon chromatographic analysis, and said compound being present in an amount sufficient to effect said treatment; together with a pharmaceutically acceptable carrier or diluent therefor other than water alone.

6. The composition of claim 5 in the form of a tablet or soft gelatin capsule.

* * * * *